United States Patent [19]

Stempel

[11] Patent Number: 5,492,943
[45] Date of Patent: Feb. 20, 1996

[54] ADHESIVE SKIN BARRIER COMPOSITION FOR OSTOMY APPLIANCE

[75] Inventor: Emil Stempel, Northbrook, Ill.

[73] Assignee: Hollister Incorporated, Libertyville, Ill.

[21] Appl. No.: 262,789

[22] Filed: Jun. 20, 1994

[51] Int. Cl.⁶ .................................................... C08L 15/00
[52] U.S. Cl. ........................... 523/111; 523/113; 524/22; 524/45; 524/55
[58] Field of Search ..................... 524/22, 45, 55, 524/502; 523/111, 113

[56] References Cited

U.S. PATENT DOCUMENTS

| | | | |
|---|---|---|---|
| 3,339,546 | 9/1967 | Chen | 128/156 |
| 4,166,051 | 8/1979 | Cilento et al. | 260/17.4 |
| 4,181,635 | 1/1980 | Takamatsu et al. | 260/5 |
| 4,192,785 | 3/1980 | Chen et al. | 260/17.4 |
| 4,204,540 | 5/1980 | Cilento et al. | 128/283 |
| 4,231,369 | 11/1980 | Sorensen et al. | 128/283 |
| 4,393,080 | 7/1983 | Pawelchak et al. | 428/355 |
| 4,551,490 | 11/1985 | Doyle et al. | 524/22 |
| 4,551,490 | 11/1985 | Doyle et al. | 524/22 |
| 4,710,182 | 12/1987 | Bryson | 604/339 |
| 4,743,499 | 5/1988 | Volke | 428/317.3 |
| 4,834,731 | 5/1989 | Nowak et al. | 604/339 |
| 4,973,323 | 11/1990 | Kaczmarek et al. | 604/339 |
| 5,059,189 | 10/1991 | Cilento et al. | 604/307 |

*Primary Examiner*—Jeffrey T. Smith
*Attorney, Agent, or Firm*—Tilton Fallon Lungmus

[57] ABSTRACT

A pressure sensitive adhesive composition particularly suitable for use as a protective skin barrier material for sealing the faceplate of an ostomy appliance, such as the faceplate of a one-piece or two-piece urostomy or an ileostomy appliance, to skin surfaces surrounding a patient's stoma. The composition includes a blend of two viscoelastic adhesive elastomers, specifically, high molecular weight polyisobutylene and a styrene block copolymer, which, along with a plasticizer (preferably petrolatum) and a suitable tackifier and antioxidant, form a continuous phase in which hydrocolloids such as sodium carboxymethylcellulose and pectin are dispersed. The composition is exceptional for its durability, flexibility and strength, even when saturated, and for its controlled swelling upon hydration.

12 Claims, No Drawings

ADHESIVE SKIN BARRIER COMPOSITION FOR OSTOMY APPLIANCE

BACKGROUND AND SUMMARY

Skin barriers are commonly used with ostomy appliances to seal the faceplates of such appliances against peristomal skin surfaces and thereby protect those surfaces from exposure to stomal effluent as well as to prevent leakage of such effluent from about the stoma-receiving openings of the pouches. Such barrier rings are usually available as integrated elements of ostomy appliances, being included as part of the adhesive faceplate of such an appliance as shown, for example, in U.S. Pat. Nos. 4,973,323; 4,834,731 and 4,710,182.

Skin barrier compositions for ostomy use should have certain physical properties, some of which have been well recognized in the past and others of which are believed now to have been discovered, or at least fully recognized, in conjunction with this invention. It has been known, for example, that barrier materials should be skin-friendly, that is, they should be soft, flexible and non-irritating to the skin and be capable of expanding and contracting in accord with body movements. They must remain adherent to the skin for extended periods but the adherence must not be so aggressive as to risk skin injury or irritation during use and upon barrier removal. A skin barrier composition should have sufficiently high cohesive strength to resist disintegration throughout its duration of use and to remain intact at the time of removal so that little or no residue remains adhered to the skin. While prior skin barrier compositions are known to achieve some of these objectives, they are also known to fall short in meeting others, particularly with respect to providing controlled hydration and sufficient strength when saturated.

Skin barrier compositions typically contain hydrocolloid particles dispersed throughout a continuous elastomeric adhesive phase. Initial tack, usually referred as "dry tack," is provided by the continuous phase but, because such a barrier is occlusive or non-breathable, adherence to the skin would be disrupted by perspiration and by liquid stomal discharge if it were not for the dispersed hydrocolloids which absorb fluids and thereby maintain and possibly enhance adhesive attachment to the skin. U.S. Pat. No. 4,551,490 and other references disclose that suitable water-absorbing and swellable hydrocolloids gums include sodium carboxymethylcellulose, pectin, gelatin, guar gum, locust bean gum, gum karaya, and mixtures thereof. The elastomers used in the continuous phase of the '490 patent are low molecular weight polyisobutylenes (having a viscosity average molecular weight from about 36,000 to about 58,000) with which butyl rubber (having a viscosity average molecular weight from about 350,000 to about 450,000) may be blended. The patentees also disclose that the elastomeric phase may contain a styrene block copolymer component to help provide extensibility and recovery from modular strains to the composition. In addition, such a composition may include mineral oil, to increase stretchability and adhesiveness of the blend, and a suitable tackifying agent and antioxidant.

A commercial skin barrier composition believed to be made in accordance with the teachings of the '490 patent is now recognized as having certain properties that compromise its usefulness as a barrier material for ostomy appliances, particularly those intended for urostomy and ileostomy use. In such an appliance, the barrier ring has an inner margin exposed to liquids discharged from the stoma into the collection pouch, resulting in liquid absorption and swelling of barrier's hydrocolloid content especially along that margin. Because of its relatively high rate of absorption, the barrier along at least a portion of the inner margin becomes saturated and the saturation front advances outwardly towards the outer margin of the barrier ring, sometimes reaching the outer margin after only a relatively short wearing interval of two days or less. Once the saturation front reaches the outer margin, leakage occurs and the faceplate (or the entire appliance if it is a one-piece appliance) must be replaced.

It is also been found that because saturation greatly reduces the cohesive strength of such a barrier material, great care must be exercised in the removal of such an appliance if tearing of the barrier ring or annular wafer is to be avoided. Should tearing occur, one particular constituent of the composition which is known to become odoriferous upon prolonged hydration becomes more exposed and particularly strong and objectionable odors are released. More serious is the fact that tearing often results in at least partial disintegration of the barrier with a portion of the ring remaining as a residue on the skin. Removal of the residue with alcohol or other solvent is not only an inconvenience but may result in irritation of the sensitive stomal and peristomal surfaces. Unfortunately, the risk of tearing is enhanced by the combination of strong wet tack of the barrier material and its and relatively low cohesive strength when saturated. Should the saturated barrier material along the inner margin of the faceplate swell into contact with the pouch or the pouch coupling ring of a two-piece appliance, then tearing of the barrier material might easily occur simply by uncoupling the pouch component. A user desiring simply to replace a pouch and having no intention of also removing the faceplate from its adhesive attachment to his/her body may suddenly find such faceplate removal is necessitated by the swelling, adhesion, and unavoidable tearing or disintegration of the skin barrier ring.

Other patents illustrative of the state of the art are U.S. Pat. Nos. 4,166,051, 4,204,540, 4,231,369, 3,339,546, 5,059,189, 4,393,080, 4,192,785, 4,743,499, and 4,181,635.

Important aspects of this invention lie in recognizing the deficencies of prior barrier compositions for ostomy use, particularly urostomy and ileostomy use, and discovering that such deficiencies may be overcome by completely avoiding the use of low molecular weight polyisobutylene and by formulating an adhesive barrier composition with an elastomer blend composed substantially entirely of one or more high molecular weight polyisobutylenes and one or more styrene block copolymers. Specifically, the polyisobutylene or polyisobutylenes in the elastomer blend should have a viscosity average molecular weight within the range of about 750,000 to 2,350,000, a preferred range being about 1,000,000 to 1,900,000. On a percentage weight basis with respect to the composition as a whole, the elastomer blend constitutes less than 25 percent of the composition with the high molecular weight polyisobutylene(s) falling within the range of about 2 to 15 percent and the styrene block copolymer(s) constituting about 5 to 20 percent. Also included in the adhesive composition is a plasticizer of either petrolatum or mineral oil (6 to 20 percent) with petrolatum being preferred. The composition additionally includes about 10 to 35 percent tackifier and up to about one percent antioxidant. The water-absorbing and swellable hydrocolloids constitute about 35 to 65 percent of the composition and are selected from the group consisting essentially of sodium carboxymethylcellulose and pectin, or mixtures thereof, and optionally include minor amounts of other hydrocolloid gums. The inclusion of gelatin is preferably avoided.

An ostomy skin barrier composition of this invention, and wafers or faceplates for ostomy appliances utilizing such composition, are noteworthy for their durability and other physical properties under real and simulated conditions of use. The weartime of a faceplate utilizing the skin barrier composition of this invention may be eight days or more, far exceeding the weartime of appliances utilizing prior barrier compositions. Such extended weartime results in part from the fact that hydration occurs more slowly and in a controlled manner, with such hydration resulting in the absorption of perspiration, with the appliance therefore remaining effectively adhered to the skin, but with the saturation front that migrates outwardly from the inner margin of the annular barrier advancing too slowly to reach the outer margin and cause leakage under normal conditions and periods of use. Even when hydrated, the composition is relatively strong and resists tearing, so that such a barrier may be more easily removed intact, without portions or fragments clinging to the skin, following extended periods of wear. When the composition is used as the barrier material for a two-piece appliance, the problems encountered in the past, in which the formation of a "turtleneck" of swollen barrier material at the inner margin of a faceplate adheres to the pouch (or pouch ring) so to become torn and require faceplate removal when a pouch is uncoupled for replacement, are eliminated or greatly reduced. Even if the skin barrier should somehow become torn following hydration, substantially less objectionable odor escapes because of the barrier formulation and, in particular, because of the absence of significant amounts of gelatin in that composition.

Other features, advantages and objects of the invention will become apparent from the specification.

DETAILED DESCRIPTION OF PREFERRED EMBODIMENTS

The pressure-sensitive adhesive compositions of this invention are particularly suitable for sealing the faceplate of an ostomy appliance to skin surfaces surrounding a patient's stoma, with such compositions having physical characteristics especially advantageous for that use. For such purposes, the composition would be formed into a wafer having a thickness of about 0.010 to 0,090 inches backed by a thin, flexible, thermoplastic backing layer along one of its faces, with such backing layer then being directly or indirectly secured to a pouch. The opposite side or face of the wafer—its bodyside surface—would be covered by a removable protective covering, such as a siliconized release sheet, until use. Ideally, the backing would be composed of a thermoplastic elastomer such as a polyurethane film, or a copolyester film of the type marketed under the designation Hytrel by DuPont (Wilmington, Del.) or polyether-block amide film marketed under the designation Pebax by Elf Atochem (Philadelphia, Pa.), but other non-elastomeric films, foams and non-woven materials may be used.

The composition is a substantially homogeneous mixture of selected components forming an adhesive viscoelastic continuous phase in which water-absorbing and swellable hydrocolloid particles are dispersed. An essential component of the continuous phase is a blend of elastomers composed substantially entirely of about 2 to 15 percent (preferably 3 to 7 percent) by weight of one more high molecular weight polyisobutylenes and about 5 to 20 percent by weight (preferably 7 to 14 percent) of one or more styrene block copolymers. "High molecular weight" here refers to a polyisobutylene having a viscosity average molecular weight within the range of about 750,000 to 2,350,000 (preferably about 1,000,000 to 1,900,000) as determined from intrinsic viscosity measurement in diisobutylene at 20 degrees C. Such polyisobutylenes are commercially available and are known, for example, under the designations Vistanex MM-L80, MM-L100, MM-L120, and MM-L140 from Exxon Corp., Houston, Tex.

A styrene block copolymer or copolymers suitable for blending with such high molecular weight polyisobutylene(s) may be identified generally as styrene-olefin-styrene block copolymers. Particularly suitable for this purpose are styrene-isoprene-styrene and styrene-butadiene-styrene block copolymers, both of which are commercially available, for example, from Shell Chemical and other suppliers. A styrene-isoprene-styrene block copolymer marketed as Kraton 1107 (Shell Chemical) is believed particularly suitable, but other Kraton copolymers, such as Kraton 1100, 1101, 1102 are also considered suitable.

Petrolatum is most advantageously used as the hydrocarbon plasticizer component in the adhesive barrier composition of this invention, although it has been found that mineral oil may also be used. Petrolatum is relatively viscous and non-flowing at room temperature, as compared to mineral oil, and these properties are believed desirable in achieving a pliant viscoelastic, and cohesive skin barrier composition. In general, the composition should contain about 6 to 20 percent by weight of petrolatum or mineral oil plasticizer, the preferred range being about 8 to 15 percent by weight.

The skin barrier compositions of this invention also include one or more water soluble hydrocolloid gums which are capable of absorbing moisture and preventing such moisture from disrupting adhesion to skin surfaces. The preferred hydrocolloid gums are sodium carboxymethylcellulose and pectin, although minor amounts of other hydrocolloid gums such as gelatin, guar gum, locust bean gum, sodium-calcium alginates, gum karaya and mixtures thereof, may be included. The hydrocolloid content of the composition should fall generally within the range of about 35 to 65 percent (preferably about 40 to 55 percent) by weight, with the preferred hydrocolloid content consisting essentially of pectin and sodium carboxymethylcellulose in a ratio of approximately 2 to 1.

The barrier composition should also contain one or more hydrocarbon tackifier resins homogeneously distributed in and forming part of the continuous phase of the composition. Particularly effective results have been obtained with an aliphatic hydrocarbon resin tackifier commercially available from Hercules Inc. (Wilmington, Del.) as Piccotac 95, although other tackifiers such as the trimethylol propane esters of rosin (Staybelite Ester 10 from Hercules) or the pentaerythritol esters of rosin (Pentalyn H from Hercules) might also be used. Other tackifiers that are believed suitable for use in the barrier composition of this invention are beta pinene or cyclopentadiene resins that are also commercially available. In general, the tackifier content should fall within the range of about 10 to 35 percent by weight, preferably about 20 to 30 percent by weight.

In addition, the barrier composition may include up to about one percent by weight of a suitable antioxidant such as Irganox 1010 or Irganox 1076 (Ciba Geigy). Other commercially-available antioxidants might also be used.

The barrier compositions of this invention are prepared by first blending the elastomers—the high molecular weight polyisobutylenes and styrene block copolymers— with antioxidant in a heavy duty mixer, such as a high shear sigma blade mixer, with heating at a temperature of about 120 degrees C. to 150 degrees C. Blending is continued with the addition of plasticizer, preferably petrolatum and, in a final blending stage, the hydrocolloids are mixed with the continuous-phase components at a temperature of about 80 degrees C. to 100 degrees C. until a homogeneous adhesive skin barrier mixture is produced. The adhesive mass is then extruded and calendered or pressed to the desired thickness (about 0.010 to 0.090 inches) on a sheet of silicone-coated release paper and a flexible backing member of thermoplastic film or other material is laminated to the other face of the adhesive barrier layer. In subsequent steps, the laminate is cut to form wafers or blankets of the desired size and shape and the backing layers are secured, preferably by heat sealing, to the walls of pouches (for one-piece appliances) or to coupling rings capable of being detachably connected to such pouches (for two-piece appliances). In either case, the wafers of skin barrier composition, backed by flexible backing layers, become the annular faceplates for adhesive sealing attachment to the peristomal skin surfaces of patients. If desired, such faceplates may be manufactured to include other features, such as the intermediate attaching ring and microporous patch of U.S. Pat. No. 4,213,458 or the floating flange construction of U.S. Pat. No. 4,419,100, the disclosures of which are incorporated by reference herein.

The following examples are further illustrative of this invention.

EXAMPLES 1–6

Pressure-sensitive skin barrier compositions embodying the invention were prepared consisting of the following ingredients on a percent weight basis:

| | Examples | | | | | |
| --- | --- | --- | --- | --- | --- | --- |
| | (1) | (2) | (3) | (4) | 5) | (6) |
| High MW polyisobutylene (Vistanex MM-L100) | 3.6 | 3.6 | 5 | 5 | 3.6 | 5 |
| Styrene-isoprene-styrene copolymer (Kraton 1107) | 8.4 | 8.4 | 8 | 5 | 8.4 | 5 |
| Petrolatum | 9.9 | 9.9 | 14.9 | 9.9 | — | 14.9 |
| Mineral Oil | — | — | — | — | 9.9 | — |
| Tackifier (Piccotac 95) | 24 | 36 | 18 | 25 | 24 | 20 |
| Antioxidant (Irganox 1010) | 0.1 | 0.1 | 0.1 | 0.1 | 0.1 | 0.1 |
| Sodium carboxymethyl-cellulose | 19 | 19 | 18 | 20 | 19 | 20 |
| Pectin | 35 | 23 | 18 | 35 | 35 | 35 |
| Gelatin | — | — | 18 | — | — | — |

The high molecular weight polyisobutylene, styrene-isopyrene-styrene copolymer, and antioxidant were blended in a sigma blade mixer with heating (at about 130 degrees C.) for approximately 10 minutes. The plasticizer (petrolatum or mineral oil) was then added to the blend and mixed for approximately 25 minutes, followed by the addition of tackifier, sodium carboxymethylcellulose and pectin and, in Example 5, gelatin. Mixing was continued at about 90 degrees C. for approximately 40 minutes until a homogeneous mass was obtained.

The mass was allowed to cool, flattened to the desired thickness on sheets of silicone-coated release paper, and cut to form wafers. In some cases the opposite surface of each wafer was covered with a film of thermoplastic elastomer (Hytrel) of 0.0012 inches thick and in other cases the opposite surface of each wafer was covered by silicone-coated release paper so that both release sheets could be removed for product testing.

EXAMPLES 7–11

Pressure-sensitive skin barrier compositions not embodying the invention but prepared for analysis on a comparative basis with Examples 1–6 contained the following ingredients on a percent weight basis:

| | Examples | | | | |
| --- | --- | --- | --- | --- | --- |
| Ingredient | (7) | (8) | (9) | (10) | 11) |
| High MW polyisobutylene (Vistanex MM-L100) | — | 13 | — | 12 | 3.6 |
| Low MW polyisobutylene (Vistanex LM-MH) | 8 | — | — | — | 24 |
| Styrene-isoprene-styrene copolymer (Kraton 1107) | 6 | — | 12 | — | 8.4 |
| Butyl 065 rubber | 16.25 | — | — | — | — |
| Petrolatum | — | 14.9 | 9.9 | 9.9 | 9.9 |
| Mineral Oil | 11.5 | — | — | — | — |
| Tackifier (Piccotac 95) | — | 18 | 24 | 24 | — |
| Tackifier (Pentalyn H) | 12.75 | — | — | — | — |
| Antioxidant (Irganox 1010) | 0.5 | 0.1 | 0.1 | 0.1 | 0.1 |
| Sodium carboxymethyl-cellulose | 15 | 18 | 19 | 19 | 19 |
| Pectin | 15 | 18 | 35 | 35 | 35 |
| Gelatin | 15 | 18 | — | — | — |

Examples 7 through 11 were prepared in accordance with the general procedure outlined in Examples 1–6. Example 7 is of the same composition disclosed in Example 1 of U.S. Pat. No. 5,059,189 and is believed to be of the same or substantially the same formulation as that of a commercial product (Durahesive).

EXAMPLE 12

In this example, the compositions of Examples 1–11 were each tested for dynamic absorption of fluid under laboratory conditions intended to simulate actual conditions of use.

For test purposes, each sample took the form of a circular wafer of 3.25 inches in diameter and a thickness of 0.070 inches covered on one side with an thermoplastic elastomeric film (Hytrel) of 0.0012 inches thick. A circular opening of 0.75 inches in diameter extended through the center of each sample, including its Hytrel backing layer. The opposite side of each wafer was secured to a double-faced adhesive mounting sheet (Avery Fasson Fast Tape 445) with an opening in register with the opening of the sample, the purpose of the mounting sheet being to permit attachment and removal of the sample from the surface of the test apparatus without damaging the sample by reason of removal forces.

The dynamic absorption test apparatus included a mounting plate of rubber having a smooth vertical surface simulating a skin surface and having a central horizontal opening therethrough simulating a stoma opening. Fluid circulation passages through the plate were connected by tubing to a pump and a heater for the circulation of water through the plate at a simulated body temperature of 35–40 degrees C. A reservoir containing water was connected by soft tubing of 1/16 inches ID to the central opening of the mounting plate and a cam-equipped peristaltic pump flexed the wall of the tubing at a frequency of 20 cycles per minute to advance water at room temperature from the reservoir into the opening of the plate at a rate of approximately 1,500 mililiters per 24 hours.

Each sample was adhered by means of the double-faced adhesive sheet to the surface of the mounting plate with its opening in register with the opening of the plate, and the apparatus was operated so that water from the reservoir would be dripped into the opening of the plate and allowed to pass through the opening of the sample. At intervals of 2, 7, 10 and 14 days, each sample of barrier material was removed and weighed to determine the cumulative weight gain by reason of water absorption. The results are tabulated below:

| | Dynamic Absorption | | | | | | | | | | |
|---|---|---|---|---|---|---|---|---|---|---|---|
| | (Weight Gain in Grams) Sample (According to Example Nos.) | | | | | | | | | | |
| Days | 1 | 2 | 3 | 4 | 5 | 6 | 7 | 8 | 9 | 10 | 11 |
| 2 | 0.24 | 0.13 | 0.12 | 0.28 | 0.4 | 0.59 | 0.67 | 0.62 | 0.54 | 0.69 | 0.58 |
| 7 | 1.7 | 0.81 | 1.15 | 1.47 | 1.35 | 3.53 | 3.66 | 2.28 | 2.62 | 2.2 | 2.31 |
| 10 | 2.83 | 1.09 | 1.82 | 2.38 | 2.16 | 4.96 | 5.33 | 3.93 | 2.98 | 3.02 | 2.92 |
| 14 | 5.2 | 1.72 | 2.69 | 4.7 | 3.73 | 6.77 | 7.76* | D | 4.04* | D | 4.61* |

Samples 1–6 utilize this invention and, with the exception of Example 6, the weight gain based on water absorption at 2 and 7 days was less than that of samples 7–11. The letter "D" indicates that samples 8 and 10 disintegrated after the 10th day and did not survive the 14 day testing cycle.

Visual inspection of sample 7 revealed that the saturation front had advanced to its outer margin by the 12th day revealing that such sample had become inoperative in preventing leakage in a radial direction from its inner to outer margins. By the 14th day, the saturation fronts for samples 9 and 11 had also reached the outer margins. The asterisks (*) for samples 7, 9 and 11 therefore denote that such samples had become inoperative in preventing leakage by or before the end of the test period. By contrast, in all of the samples 1–6, the saturation fronts had advanced more slowly in radial directions and not reached the outer margins by the end of the 14-day test period.

With regard to samples 1 and 7, the test results are consistent with what has been observed clinically. Sample 1 is a wafer having an adhesive compositon of this invention as it now appears in a commerical product and sample 7 is believed to be representative of a barrier product (Durahesive) that does not embody this invention but is also commercially available. Clinical investigations support the observation that in actual practice wafers having a composition corresponding to that of sample 7 absorbs more fluid, with the saturation fronts advancing more rapidly to the outer margins and substantially reducing the weartime by several days, in comparison with wafers having the composition of sample 1.

EXAMPLE 13

This example reveals the results of tests on the samples of Examples 1 through 11 when such samples (with Hytrel backings and release paper removed) were immersed in simulated urine and their weight gain in grams was measured at intervals of 1, 6 and 24 hours. The following results were obtained:

| | Absorption of Simulated Urine | | | | | | | | | | |
|---|---|---|---|---|---|---|---|---|---|---|---|
| | (Weight Gain in Grams) Sample (According to Example Nos.) | | | | | | | | | | |
| Hours | 1 | 2 | 3 | 4 | 5 | 6 | 7 | 8 | 9 | 10 | 11 |
| 1 | 1.4 | 0.9 | 1 | 1.6 | 1.3 | 1.3 | 1.1 | 1.9 | 1.6 | 2.3 | 1.1 |
| 6 | 2.4 | 1 | 2.3 | 2.8 | 2.5 | 2.2 | 2.7 | 6.9 | 3.5 | 6.9 | 3.3 |
| 24 | 5.5 | 1.8 | 5.1 | 5.6 | 5.5 | 4.7 | 5.7 | 10.5 | 5.6 | 11.8 | 7 |

EXAMPLE 14

The tensile properties of the barrier compositions of Examples 1 through 11 were tested on an Instron machine (Type 4501) and the stress and strain of each sample was measured both at peak and at break. In addition, the stresses at 10 percent, 20 percent and 50 percent strain were measured.

For purposes of such testing, strips of barrier material without backing were cut, each strip having a width of half an inch. The ends of each strip were placed in the jaws of the machine at an initial separation of one inch, and the jaws were separated at a crosshead speed of 2.5 inches per minute. The tests produced the following data revealing the tensile or cohesive strength of the respective barrier materials:

| | Tensile Properties | | | | | | | | | | |
|---|---|---|---|---|---|---|---|---|---|---|---|
| | Examples (According to Example Nos.) | | | | | | | | | | |
| | 1 | 2 | 3 | 4 | 5 | 6 | 7 | 8 | 9 | 10 | 11 |
| Stress @ peak (psi) | 14.7 | 16.6 | 7.9 | 9.3 | 11.4 | 5.8 | 6.8 | 15 | 32.5 | 10 | 8.1 |
| Strain @ peak (%) | 224 | 450 | 158 | 46 | 207 | 43 | 39 | 46 | 238 | 34 | 41 |
| Stress @ break | 9.1 | 11.8 | 5.4 | 3.4 | 8.5 | 2 | 4.1 | 5.1 | 17.1 | — | 3.1 |

-continued

|  | Tensile Properties | | | | | | | | | | |
|---|---|---|---|---|---|---|---|---|---|---|---|
|  | Examples (According to Example Nos.) | | | | | | | | | | |
|  | 1 | 2 | 3 | 4 | 5 | 6 | 7 | 8 | 9 | 10 | 11 |
| (psi) Strain @ break (psi) | 657 | 876 | 445 | 1146 | 530 | 541 | 793 | 548 | 343 | — | 215 |
| Stress @ 10% strain (psi) | 5 | 5.4 | 2.2 | 4.8 | 3.7 | 2.9 | 2.6 | 10.1 | 5.7 | 6.2 | 4 |
| Stress @ 20% strain (psi) | 7.5 | 7.2 | 4.1 | 7.2 | 5.8 | 4.4 | 4.8 | 13.3 | 9.2 | 8.5 | 6.3 |
| Stress @ 50% strain (psi) | 10.9 | 9.2 | 6.3 | 9.1 | 8.8 | 5.6 | 6.7 | 14.7 | 15 | 9.9 | 7.9 |

EXAMPLE 15

For purposes of measuring compression set for the barrier compositions of Examples 1–11, one inch diameter samples of each barrier material were cut. Then the samples between release paper were placed on a hard level surface in an oven set at 60 degrees C. and 5 kg weights were placed on each sample. After one hour, the samples were removed from the oven and their diameters were measured to the nearest thousandths of an inch at four locations: 0, 45, 90 and 135 degrees. The average of such measurements was computed for each sample and the compression set at one hour, as a percentage of the original diameter, was calculated as follows:

$$\frac{D_2 - D_1}{D_1} \times 100 = \text{Compression Set (\%)}$$

where $D_1$ represents original diameter and $D_2$ represents average final diameter.

| Compression Set | | | | | | | | | | |
|---|---|---|---|---|---|---|---|---|---|---|
| (% of Original Diameter Increase) Samples (According to Example Nos.) | | | | | | | | | | |
| 1 | 2 | 3 | 4 | 5 | 6 | 7 | 8 | 9 | 10 | 11 |
| 42 | 50 | 40 | 33 | 58 | 57 | 58 | 58 | 25 | 49 | 53 |

While in the foregoing, embodiments of the invention have been disclosed in considerable detail for purposes of illustration, it will be understood by those skilled in the art that many of these details may be varied without departing from the spirit and scope of the invention.

I claim:

1. A pressure-sensitive adhesive skin barrier composition particularly suitable for use in sealing the faceplate of an ostomy appliance to skin surfaces surrounding a patient's stoma, consisting essentially of a substantially homogeneous mixture on a percent weight basis of an elastomer blend essentially composed of about 2 percent to about 15 percent of one or more high molecular weight polyisobutylenes and about 5 percent to about 20 percent of one or more styrene block copolymers, said one or more polyisobutylenes of said blend being only of a viscosity average molecular weight within the range of about 750,000 to about 2,350,000; about 6 percent to about 20 percent of hydrocarbon plasticizer selected from the group consisting of petrolatum and mineral oil; about 10 percent to about 35 percent tackifier; up to about 1 percent antioxidant; and about 35 percent to about 65 percent water-absorbing hydrocolloids selected from the group consisting of sodium carboxymethylcellulose, pectin, and mixtures thereof, and optionally including minor amounts of other hydrocolloid gums.

2. The composition of claim 1 in which said one or more high molecular weight polyisobutylenes each has a viscosity average molecular weight within the range of about 1,000,000 to about 1,900,000.

3. The composition of claims 1 or 2 in which said plasticizer is petrolatum.

4. The composition of claims 1 or 2 in which said one or more styrene block copolymers comprises a styrene-isoprene-styrene block copolymer.

5. The composition of claims 1 or 2 in which said elastomer blend is essentially composed of about 3 percent to about 7 percent of one or more of said high molecular weight polyisobutylenes and about 7 percent to about 14 percent of one or more of said styrene block copolymers.

6. The composition of claims 1 or 2 in which said hydrocarbon plasticizer consists essentially of about 8 percent to about 15 percent petrolatum.

7. The composition of claims 1 or 2 in which said hydrocolloids consist of about 40 percent to about 55 percent of said composition and consist essentially of a mixture of sodium carboxymethylcellulose and pectin.

8. The composition of claims 1 or 2 in which there is from about 20 percent to about 30 percent of said tackifier.

9. A flat wafer formed of the adhesive composition of claims 1 or 2, said wafer having a thickness of about 0.010 inches to about 0.090 inches and having a thin flexible polymeric backing layer adhered to one side thereof.

10. The wafer of claim 9 in which said polymeric backing layer is elastomeric.

11. A pressure-sensitive adhesive skin barrier composition particularly suitable for use in sealing the faceplate of an ostomy appliance to skin surfaces surrounding a patient's stoma, consisting essentially of a substantially homogeneous mixture on a percent weight basis of an elastomer blend essentially composed of about 3 percent to about 7 percent of one or more high molecular weight polyisobutylenes and about 7 percent to about 14 percent of one or more styrene block copolymers, said one or more polyisobutylenes of said blend being only of a viscosity average molecular weight within the range of 750,000 to about 2,350,000; about 8 percent to about 15 percent petrolatum; about 20 percent to about 30 percent tackifier; up to about 1 percent antioxidant; and about 35 percent to about 65 percent water-absorbing hydrocolloids selected from the group consisting of sodium carboxymethylcellulose, pectin, and mixtures thereof, and optionally including minor amount of other hydrocolloid gums.

12. The composition of claim 11 in which said one or more high molecular weight polyisobutylenes each has a viscosity average molecular weight within the range of about 1,000,000 to about 1,900,000.

* * * * *